US008338375B2

(12) United States Patent
Schroeder et al.

(10) Patent No.: US 8,338,375 B2
(45) Date of Patent: Dec. 25, 2012

(54) PACKAGED PRODUCT

(75) Inventors: Jacqueline Anne Schroeder, Boulder Creek, CA (US); Gregory S. Dapper, Newark, CA (US); Kenneth C. Olson, Foster City, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 12/649,020

(22) Filed: Dec. 29, 2009

(65) Prior Publication Data
US 2010/0099624 A1 Apr. 22, 2010

Related U.S. Application Data

(62) Division of application No. 12/125,337, filed on May 22, 2008.

(60) Provisional application No. 60/939,664, filed on May 23, 2007.

(51) Int. Cl.
*A61K 8/65* (2006.01)
(52) U.S. Cl. .............................. 514/12; 514/2
(58) Field of Classification Search ........................ None
See application file for complete search history.

(56) References Cited

U.S. PATENT DOCUMENTS

| 2,128,827 | A | 8/1938 | Killian |
|---|---|---|---|
| 3,548,056 | A | 12/1970 | Eigen et al. |
| 3,763,009 | A | 10/1973 | Suzuki |
| 3,949,073 | A | 4/1976 | Daniels et al. |
| 4,060,081 | A | 11/1977 | Yannas et al. |
| 4,140,537 | A | 2/1979 | Luck et al. |
| 4,233,360 | A | 11/1980 | Luck et al. |
| 4,273,705 | A | 6/1981 | Kato |
| 4,279,812 | A | 7/1981 | Cioca |
| 4,424,208 | A | 1/1984 | Wallace et al. |
| 4,501,306 | A | 2/1985 | Chu et al. |
| 4,582,640 | A | 4/1986 | Smestad et al. |
| 4,582,865 | A | 4/1986 | Balazs et al. |
| 4,605,691 | A | 8/1986 | Balazs et al. |
| 4,636,524 | A | 1/1987 | Balazs |
| 4,642,117 | A | 2/1987 | Nguyen et al. |
| 4,713,448 | A | 12/1987 | Balazs |
| 4,716,154 | A | 12/1987 | Malson et al. |
| 4,803,075 | A | 2/1989 | Wallace et al. |
| 4,886,787 | A | 12/1989 | De Belder et al. |
| 4,896,787 | A | 1/1990 | Delamour et al. |
| 5,009,013 | A | 4/1991 | Wiklund |
| 5,087,446 | A | 2/1992 | Suzuki et al. |
| 5,091,171 | A | 2/1992 | Yu et al. |
| 5,143,724 | A | 9/1992 | Leshchiner et al. |
| 5,246,698 | A | 9/1993 | Leshchiner et al. |
| 5,314,874 | A | 5/1994 | Miyata et al. |
| 5,328,955 | A | 7/1994 | Rhee et al. |
| 5,356,883 | A | 10/1994 | Kuo et al. |
| 5,399,351 | A | 3/1995 | Leshchiner et al. |
| 5,428,024 | A | 6/1995 | Chu et al. |
| 5,531,716 | A | 7/1996 | Luzio et al. |
| 5,565,519 | A | 10/1996 | Rhee et al. |
| 5,571,503 | A | 11/1996 | Mausner |
| 5,614,587 | A | 3/1997 | Rhee et al. |
| 5,616,568 | A | 4/1997 | Pouyani et al. |
| 5,616,611 | A | 4/1997 | Yamamoto |
| 5,616,689 | A | 4/1997 | Shenoy et al. |
| 5,633,001 | A | 5/1997 | Agerup |
| 5,643,464 | A | 7/1997 | Rhee et al. |
| 5,676,964 | A | 10/1997 | della Valle |
| 5,823,671 | A | 10/1998 | Mitchell et al. |
| 5,824,333 | A | 10/1998 | Scopelianos et al. |
| 5,827,529 | A | 10/1998 | Ono et al. |
| 5,843,907 | A | 12/1998 | Sakai |
| 5,880,107 | A | 3/1999 | Buenter |
| 5,886,042 | A | 3/1999 | Yu et al. |
| 5,935,164 | A | 8/1999 | Iversen |
| 5,980,930 | A | 11/1999 | Fenton et al. |
| 6,013,679 | A | 1/2000 | Kuo et al. |
| 6,066,325 | A | 5/2000 | Wallace et al. |
| 6,224,857 | B1 | 5/2001 | Romeo et al. |
| 6,335,035 | B1 | 1/2002 | Drizen et al. |
| 6,372,494 | B1 | 4/2002 | Naughton et al. |
| 6,383,218 | B1 | 5/2002 | Sourdille et al. |
| 6,383,219 | B1 | 5/2002 | Telandro et al. |
| 6,418,934 | B1 | 7/2002 | Chin |
| 6,521,223 | B1 | 2/2003 | Calias et al. |
| 6,544,503 | B1 | 4/2003 | Vanderhoff et al. |
| 6,627,620 | B1 | 9/2003 | Nielsen |

(Continued)

FOREIGN PATENT DOCUMENTS
CA 949965 6/1974
(Continued)

OTHER PUBLICATIONS

Grillo, Hermes C., et al., "Thermal Reconstitution of Collagen from Solution and the Response to Its Heterologous Implantation," J.S.R., II, No. 1, pp. 69-82 (1962).
Chvapil, Milos, "Collagen Sponse: Theory and Practice of Medical Applications," J. Biomed Mater. Res., II, pp. 721-741 (1977).
Bluel, K.E., et al., "Evaluation of Reconstituted Collagen Tape as a Model for Chemically Modified Soft Tissues," Biomat., Med. Dev., Art. Org., 9(1), pp. 37-46 (1981).
McPherson, J., et al., "Development and Biochemical Charaterization of Injectable Collagen," J Dermatol Surg Oncol 14, Supp. Jul. 1, 1988, pp. 13-20.
Rosenblatt, J., et al., "The Effect of Collagen Fiber Size Distribution on the Release Rate of Proteins from Collagen Matrices by Diffusion," J. Controlled Rel., 9, pp. 195-203 (1989).
Rosenblatt, et al., "Chain Rigidity and Diffusional Release in Biopolymer Gels," Proceed. Intern. Symp. Control. Rel. Bioact. Mater., 20, pp. 264-265 (1993) Controlled Release Society, Inc.
Klein, Arnold William, M.D. "Skin Filling Collagen and Other Injectables of the Skin," Dematologic Clinics Jul. 2001, vol. 19, No. 3, pp. 491-588, ix, XP00919589.

(Continued)

*Primary Examiner* — Hope A. Robinson
(74) *Attorney, Agent, or Firm* — Linda Allyson Fox; Stephen Donovan; Debra Condino (57) ABSTRACT

The present invention discloses collagen cross-linked in a micro to non-fibrillar form and at a high concentration. The cross-linked collagen gel has improved volume stability or persistence than collagen cross-linked at a neutral pH. Also disclosed are methods for preparing the inventive cross-linked collagen and using such for augmenting soft tissues in mammals.

12 Claims, 2 Drawing Sheets

U.S. PATENT DOCUMENTS

| | | |
|---|---|---|
| 6,630,486 B1 | 10/2003 | Royer |
| 6,685,963 B1 | 2/2004 | Taupin et al. |
| 6,716,251 B1 | 4/2004 | Asius et al. |
| 6,734,298 B1 | 5/2004 | Barbucci |
| 6,767,924 B2 | 7/2004 | Yu et al. |
| 6,767,928 B1 | 7/2004 | Murphy et al. |
| 6,852,255 B2 | 2/2005 | Yang |
| 6,893,466 B2 | 5/2005 | Trieu |
| 6,903,199 B2 | 6/2005 | Moon |
| 6,921,819 B2 | 7/2005 | Piron et al. |
| 6,924,273 B2 | 8/2005 | Pierce |
| 6,939,562 B2 | 9/2005 | Spiro et al. |
| 6,979,440 B2 | 12/2005 | Shefer et al. |
| 7,119,062 B1 | 10/2006 | Alvis et al. |
| 7,166,570 B2 * | 1/2007 | Hunter et al. ............... 514/21.92 |
| 7,192,984 B2 | 3/2007 | Berg |
| 7,196,180 B2 | 3/2007 | Aeschlimann |
| 7,314,636 B2 | 1/2008 | Caseres et al. |
| 7,491,709 B2 | 2/2009 | Carey |
| 7,741,476 B2 | 6/2010 | Lebreton |
| 7,902,171 B2 | 3/2011 | Reinmuller et al. |
| 8,124,120 B2 | 2/2012 | Sadozai |
| 2002/0102311 A1 | 8/2002 | Gustavsson et al. |
| 2002/0160109 A1 | 10/2002 | Yeo et al. |
| 2003/0031638 A1 | 2/2003 | Joshi et al. |
| 2003/0093157 A1 | 5/2003 | Casares et al. |
| 2003/0119985 A1 | 6/2003 | Sehl et al. |
| 2003/0148995 A1 | 8/2003 | Piron et al. |
| 2004/0032056 A1 | 2/2004 | Vang et al. |
| 2004/0101959 A1 | 5/2004 | Marko et al. |
| 2004/0127698 A1 | 7/2004 | Tsai et al. |
| 2004/0127699 A1 | 7/2004 | Zhao et al. |
| 2004/0199241 A1 | 10/2004 | Gravett et al. |
| 2004/0265389 A1 | 12/2004 | Yui et al. |
| 2005/0101582 A1 | 5/2005 | Lyons et al. |
| 2005/0136122 A1 | 6/2005 | Sadozai et al. |
| 2005/0142152 A1 | 6/2005 | Leshchiner et al. |
| 2005/0181007 A1 | 8/2005 | Hunter |
| 2005/0186261 A1 | 8/2005 | Avelar |
| 2005/0226936 A1 | 10/2005 | Agerup |
| 2005/0271729 A1 | 12/2005 | Wang |
| 2005/0287180 A1 | 12/2005 | Chen |
| 2006/0040894 A1 | 2/2006 | Hunter et al. |
| 2006/0095137 A1 | 5/2006 | Chung et al. |
| 2006/0122147 A1 | 6/2006 | Wohlrab |
| 2006/0141049 A1 | 6/2006 | Lyons et al. |
| 2006/0147483 A1 | 7/2006 | Chaouk et al. |
| 2006/0194758 A1 | 8/2006 | Lebreton |
| 2006/0246137 A1 | 11/2006 | Hermitte et al. |
| 2006/0257488 A1 | 11/2006 | Hubbard |
| 2006/0286769 A1 | 12/2006 | Tsuchiya et al. |
| 2007/0077292 A1 | 4/2007 | Pinsky |
| 2007/0203095 A1 | 8/2007 | Sadozai et al. |
| 2007/0212385 A1 | 9/2007 | David |
| 2007/0224247 A1 | 9/2007 | Chudzik |
| 2007/0224278 A1 | 9/2007 | Lyons et al. |
| 2007/0298005 A1 | 12/2007 | Thibault |
| 2008/0044476 A1 | 2/2008 | Lyons et al. |
| 2008/0057091 A1 | 3/2008 | Abdellaoui |
| 2008/0089918 A1 | 4/2008 | Lebreton |
| 2008/0188416 A1 | 8/2008 | Bernstein |
| 2008/0193538 A1 | 8/2008 | Kitazono et al. |
| 2008/0200430 A1 | 8/2008 | Bitterman et al. |
| 2008/0207794 A1 | 8/2008 | Wright et al. |
| 2008/0241252 A1 | 10/2008 | Lyons |
| 2008/0268051 A1 | 10/2008 | Lyons |
| 2008/0274946 A1 | 11/2008 | Gimpapa |
| 2008/0279806 A1 | 11/2008 | Cho |
| 2009/0018102 A1 | 1/2009 | Moutet |
| 2009/0022808 A1 | 1/2009 | Champion |
| 2009/0028817 A1 | 1/2009 | Niklason et al. |
| 2009/0036403 A1 | 2/2009 | Stroumpolis et al. |
| 2009/0042834 A1 | 2/2009 | Karageozian et al. |
| 2009/0093755 A1 | 4/2009 | Schroeder |
| 2009/0110671 A1 | 4/2009 | Miyata et al. |
| 2009/0110736 A1 | 4/2009 | Boutros |
| 2009/0143331 A1 | 6/2009 | Stroumpoulis et al. |
| 2009/0143348 A1 | 6/2009 | Tezel |
| 2009/0148527 A1 | 6/2009 | Robinson |
| 2009/0155314 A1 | 6/2009 | Tezel |
| 2009/0155362 A1 | 6/2009 | Longin |
| 2009/0169615 A1 | 7/2009 | Pinsky |
| 2009/0291986 A1 | 11/2009 | Pappas et al. |
| 2009/0297632 A1 | 12/2009 | Waugh |
| 2010/0004198 A1 | 1/2010 | Stroumpoulis et al. |
| 2010/0028437 A1 | 2/2010 | Lebreton |
| 2010/0035838 A1 | 2/2010 | Heber et al. |
| 2010/0041788 A1 | 2/2010 | Voigts et al. |
| 2010/0098764 A1 | 4/2010 | Stroumpoulis et al. |
| 2010/0098794 A1 | 4/2010 | Armand |
| 2010/0099623 A1 | 4/2010 | Schroeder et al. |
| 2010/0111919 A1 | 5/2010 | Abuzaina et al. |
| 2010/0136070 A1 | 6/2010 | Dobak et al. |
| 2010/0226988 A1 | 9/2010 | Lebreton |
| 2010/0316683 A1 | 12/2010 | Piron |
| 2011/0034684 A1 | 2/2011 | Yokokawa |

FOREIGN PATENT DOCUMENTS

| | | |
|---|---|---|
| EP | 0273823 | 7/1988 |
| EP | 0416250 | 3/1991 |
| EP | 0416846 | 3/1991 |
| EP | 1247522 | 10/2002 |
| EP | 141792 | 4/2003 |
| EP | 1419792 | 4/2003 |
| EP | 1398131 | 3/2004 |
| EP | 1726299 | 11/2006 |
| FR | 2733427 | 10/1996 |
| FR | 2920000 | 2/2009 |
| FR | 2924615 | 6/2009 |
| JP | 55-153711 | 11/1980 |
| JP | 2007063177 | 3/2007 |
| WO | WO 86/00079 | 1/1986 |
| WO | WO 86/00912 | 2/1986 |
| WO | WO 92/00105 | 1/1992 |
| WO | WO 92/20349 | 11/1992 |
| WO | WO 94/01468 | 1/1994 |
| WO | WO 94/02517 | 2/1994 |
| WO | WO 96/33751 | 1/1996 |
| WO | WO 97/04012 | 2/1997 |
| WO | WO 98/35639 | 8/1998 |
| WO | WO 98/35640 | 8/1998 |
| WO | WO 00/01428 | 1/2000 |
| WO | WO 01/79342 A2 | 10/2001 |
| WO | WO 02/05753 | 1/2002 |
| WO | WO 02/06350 | 1/2002 |
| WO | WO 02/09792 | 2/2002 |
| WO | WO 02/17713 | 3/2002 |
| WO | WO 03/007782 | 1/2003 |
| WO | WO 2004/020473 | 3/2004 |
| WO | WO 2004/022603 | 3/2004 |
| WO | WO 2004/073759 | 9/2004 |
| WO | WO 2004/092223 | 10/2004 |
| WO | WO 2005/040224 | 5/2005 |
| WO | WO 2005/067944 | 7/2005 |
| WO | WO 2005/074913 | 8/2005 |
| WO | WO 2005/112888 | 12/2005 |
| WO | WO 2006/023645 | 3/2006 |
| WO | WO 2006/067608 | 6/2006 |
| WO | WO 2007/018124 | 2/2007 |
| WO | WO 2007/070617 | 6/2007 |
| WO | WO 2007/077399 | 7/2007 |
| WO | WO 2007/128923 | 11/2007 |
| WO | WO 2008/034176 | 3/2008 |
| WO | WO 2008/068297 | 6/2008 |
| WO | WO 2008/072230 | 6/2008 |
| WO | WO 2008/077172 | 7/2008 |
| WO | WO 2008/098019 | 8/2008 |
| WO | WO 2008/139122 | 11/2008 |
| WO | WO 2008/148967 | 12/2008 |
| WO | WO 2008/157608 | 12/2008 |
| WO | WO 2009/024719 | 2/2009 |
| WO | WO 2009/028764 | 3/2009 |
| WO | WO 2009/034559 | 3/2009 |
| WO | WO 2009/073437 | 6/2009 |
| WO | WO 2010/003797 | 1/2010 |
| WO | WO 2010/015900 | 2/2010 |
| WO | WO 2010/027471 | 3/2010 |

| WO | WO 2010/028025 | 3/2010 |
| WO | WO 2010/029344 | 3/2010 |
| WO | WO 2010/038771 | 4/2010 |
| WO | WO 2010/051641 | 5/2010 |
| WO | WO 2010/052430 | 5/2010 |
| WO | WO 2010/061005 | 6/2010 |

OTHER PUBLICATIONS

Eyre, et al. "Collagen Cross-Links," Top Curr Chem (2005) vol. 247, pp. 207-229.
Millay et al.; "Vasoconstrictors in Facial Plastic Surgery"; Archives of Otolaryngology—Head & Neck Surgery; vol. 117; pp. 160-163; Feb. 1991.
Wahl, "European Evaluation of a New Hyaluronic Acid Filler Incorporating Lidocaine", Journal of Cosmetic Dermatology; vol. 7; pp. 298-303; 2008.
Aesthetic Buyers Guide, "Juvéderm Raises Standards"; Jan./Feb. 2007 (5 pp.), www.miinews.com.
Adams; "An Analysis of Clinical Studies of the Uses of Crosslinked Hyaluronan, Hylan, in the Treatment of Osteoarthritis"; J. Rheumatol Suppl. ; vol. 39; pp. 16-18; Aug. 1993.
Albano et al.; "Hyroxyethyl Radicals in Ethanol Hepatotoxicity"; Frontiers in Bioscience; vol. 4; pp. 533-540; 1999.
Allemann et al.; "Hyaluronic acid gel (JUVADERM) preparations in the treatment of facial wrinkles and folds"; Clinical Interventions in Aging; vol. 3, No. 4; pp. 629-634; 2008.
Antunes et al.; "Efficacy of Intrarectal Lidocaine Hydrochloride Gel for Pain control in Patients Undergoing Transrectal Prostate Biopsy"; International Braz J Urol; vol. 30, No. 5; pp. 380-383; Sep.-Oct. 2004.
Atanassoff et al.; "The Effect of Intradermal Administration of Lidocaine and Morphine on the Response to Thermal Stimulation"; Anesth Analg; vol. 84; pp. 1340-1343; 1997.
Baumann et al.; "Comparison of smooth-gel hyaluronic acid dermal fillers with cross-linked bovine collagen: a multicenter, double-masked, randomized, within-subject study"; Dermatol. Surg.; vol. 33(Suppl 2); pp. S128-S135 2007.
Beasley et al.; "Hyaluronic acid fillers: a comprehensive review"; Facial Plast. Surg.; vol. 25, No. 2; pp. 86-94; 2009.
Beer; "Dermal fillers and combinations of fillers for facial rejuvenation"; Dermatol. Clin.; vol. 27, No. 4; pp. 427-432; 2009.
Belda et al.; "Hyaluronic acid combined with mannitol to improve protection against free-radical endothelial damage: Experimental Model"; J.Cataract Refract Surg; Vo. 31; pp. 1213-1218; 2005.
Bircher, et al.; "Delayed-Type Hypersensitivity to Subcutaneous Lidocaine With Tolerance to Articaine: Confirmation by In Vivo and In Vitro Tests"; Contact Dermatitis; vol. 34; pp. 387-389; 1996.
Capozzi et al., "Distant Migration of Silicone Gel From a Ruptured Breast Implant", Plastic and Reconstructive Surgery; vol. 62; pp. 302-303; 1978.
Carlin et al., "Effect of anti-inflammatory drugs on xanthine oxidase and xanthine oxidase induced depolymerization of hyaluronic acid"; Agents and Actions; vol. 16 (5); pp. 377-384; 1985.
Carruthers et al.; "The science and art of dermal fillers for soft-tissue augmentation"; J. Drugs Dermatol; vol. 8(4); pp. 335-350; 2009.
Champion et al., "Role of Target Geometry in Phagocytosis"; S. Proc. Nat. Acad. Sci.; vol. 103; No. 13; pp. 4930-4934; Mar. 28, 2006.
Chin et al., "Allergic Hypersensitivity to Lidocaine Hydrochloride", International journal of Dermatology, vol. 19; pp. 147-148; Apr. 1980.
Clark et al., "The Influence of Triamcinolone Acetonide on Joint Stiffness in the Rat", J Bone Joint Surg; vol. 53-A; pp. 1409-1414; Oct. 1971.
Cohen et al., "Organization and Adhesive Properties of the Hyaluronan Pericellular Coat of Chrondrocytes and Epithelial Cells", Biophys J.; vol. 85; pp. 1996-2005; Sep. 2003.
Deland, "Intrathecal Toxicity Studies with Benzyl Alcohol", Toxicol Appl Pharmacol; vol. 25; pp. 153-156; 1973.
Desai et al., J Pharm Sci Abstract only; 84 (2): 212-215; Feb. 1995.
Falcone et al.; "Crosslinked hyaluronic acid dermal fillers: a comparison of rheological properties." J Biomed Mater Res; vol. 87(1); pp. 264-271; 2008.

Falcone et al.; "Temporary polysaccharide dermal fillers: a model for persistence based on physical properties." Dermatol Surg.; vol. 35(8); pp. 1238-1243; 2009.
Farley et al., "Diluting Lidocaine and Mepivacaine in Balanced Salt Solution Reduces the Pain of Intradermal Injection", Regional Anesthesia; vol. 19(1); pp. 48-51; 1994.
Frati et al., "Degradation of hyaluronic acid by photosensitized riboflavin in vitro. Modulation of the effect by transition metals, radical quenchers, and metal chelators"; Free Radical Biology Medicine; vol. 22 (7); pp. 1139-1144 1997.
Fujinaga et al., "Reproductive and Teratogenic Effects of Lidocaine in Sprague-Dawley Rats"; Anesthesiology vol. 65; pp. 626-632; 1986.
Gammaitoni et al., "Pharmacokinetics and safety of continuously applied lidocaine patches 5%", Am J Health Syst Pharm; vol. 59; pp. 2215-2220; Nov. 15, 2002.
GinShiCel MH Hydroxy Propyl methyl Cellulose, Web Page http://www.ginshicel.cn/MHPC.html, Nov. 12, 2008.
Gold; "Use of Hyaluronic acid fillers for the treatment of the aging face"; Clin. Interventions Aging; vol. 2(3); pp. 369-376; 2007.
Goldberg; "Breakthroughs in US dermal fillers for facial soft-tissue augmentation"; J Cosmet Laser Ther; vol. 11; pp. 240-247; 2009.
Graefe et al., "Sensitive and specific photometric determination of mannitol in human serum"; Clin Chem Lab Med; vol. 41, No. 8; pp. 1049-1055; 2003.
Grecomoro et al., "Intra-Articular Treatment with Sodium Hyaluronate in Gonarthosis: A Controlled Clinical Trial Versus Placebo", Pharmatherapeutica, vol. 5(2); pp. 137-141; 1987.
Hassan et al., "Effects of Adjuvants to local anaesthetics on their duration. III. Experimental studies of hyaluronic acid"; Abstract Pub Med [Acta Anesthesiol Scand; vol. 29(4); pp. 384-388; May 1985.
Hayashibara, "AA2G"; Sep. 23, 2007, http://web.archive.org/web/20079230720l0/http://www.hayashibara-intl.com/cosmetics/aa2g.html.
Helliwell, "Use of an Objective Measure of Articular Stiffness to Record Changes in Finger Joints After Intra-Articular Injection of Corticosteroid", An Theum Dis; vol. 56; pp. 71-73; 1997.
Hertzberger-Ten Cate et al., "Intra-Articular Steroids in Pauciarticular Juvenile Chronic Arthritis", Type I, Eur J Pediatr; vol. 150; pp. 170-172; 1991.
Hetherington, "Potential for Patient Harm From Intrathecal Administration of Preserved Solutions", Abstract only Med J; vol. 173(3); p. 141; Aug. 2000.
Hurst, "Adhesive Arachnoiditis and Vascular Blockage Caused by Detergents and Other Chemical Irritants: an Experimental Study", J Path Bact, vol. LXX, No. 70; pp. 167-177; 1955.
Intramed Mannitol 20% m/v Infusion, package insert, pp. 1-2 (2010) http://home.intekom.com/pharm/intramed/manitl20.html.
Jones et al., "Intra-Articular Hyaluronic Acid Compared to Intra-Articular Triamcinolone Hexacetonide in Inflammatory Knee Osteoarthritis", Osteoarthritis Cartilage, vol. 3; pp. 269-273; 1995.
Kablik et al. "Comparative physical properties of hyaluronic acid dermal fillers." Dermatol. Surg.; vol. 35(Suppl. 1); pp. 302-312; 2009.
Kopp et al., "The Short-Term Effect of Intra-Articular Injections of Sodium Hyaluronate and Corticosteroid on Temporomandibular Joint Pain and Dysfunction"; J. Oral Maxillofac Surg.; V. 43; pp. 429-435; 1985.
Kulicke et al., "Visco-Elastic Properties of Sodium Hyaluronate Solutions," American Institue of Physics; 3 pages; 2008.
Laeschke, "Biocompatibility of Microparticles into Soft Tissue Fillers", Semin. Cutan. Med. Surg., vol. 23; pp. 214-217; 2004.
Lamar et al., "Antifibrosis Effect of Novel Gels in Anterior Ciliary Slerotomy (ACS)," ARVO 2002 abstract only.
Levy et al., "Lidocaine hypersensitivity after subconjunctival injection", Can J Ophthalmol 2006; vol. 41, No. 2; pp. 204-206.
Lupo; "Hyaluronic acid fillers in facial rejuvenation." Semin. Cutan. Med. Surg.; vol. 25; pp. 122-126; 2006.
Mackley et al., "Delayed-Type Hypersensitivity to Lidocaine", Arch Dermatol, vol. 139; pp. 343-346; Mar. 2003.
Mancinelli et al., "Intramuscular High-Dose Triamcinolone Acetonide in the Treatment of Severe Chronic Asthma", West J. Med; vol. 167(5); pp. 322-329; Nov. 1997.

Matsumoto et al., "Reducing the Discomfort of Lidocaine Administration through pH Buffering," Journal of Vascular and Interventional Radiology; vol. 5, No. 1; pp. 171-175; Nov. 1997.

McCarty et al., "Inflammatory Reaction After Intrasynovial Injection of Microcrystalline Adrenocorticosteroid Esters", Arthritis and Rheuymatism; vol. 7(4); pp. 359-367; 1964.

McCleland et al.; "Evlaution of Artecoll Polymethacrylate Implant for Soft-Tissue Augmentation: Biocompatibility and Chemical Chartacterization"; Plastric Reconstructive Surgery; vol. 100(6); pp. 1466-1474; Nov. 1997.

Orvisky et al., "High-molecular-weight hyaluronan—a valuable tool in testing the antioxidative activity of amphiphilic drugs stobadine and vinpocetine"; J. Pharm. Biomed. Anal.; vol. 16; pp. 419-424; 1997.

Osmitrol (generic name Mannitol),Official FDA Information, side effects and uses, pp. 1-10 (2010) http://www.drugs.com/pro/osmitrol.html.

Prestwich; "Evaluating drug efficacy and toxicology in three dimensions: using synthetic extracellular matrices in drug discovery"; Accounts of Chemical Research; vol. 41, No. 1; pp. 139-148; Jan. 2008.

Rehakova et al.; "Properties of collagen and hyaluronic acid composite materials and their modifications by chemical crosslinking," Journal of Biomedical Materials Research; vol. 30; pp. 369-372; 1996.

Remington's Pharmaceutical Science Mac Publishing Company, Easton, PA 16th Edition 1980; 1-page.

Sannino et al., "Crosslinking of Cellulose Derivatives and Hyaluronic Acid with Water-Soluble Carbodiimide," Polymer; vol. 46; pp. 11206-11212 ; 2005.

Sculptra® Aesthetic (injectable poly-L-lactic acid) Directions for Use, Dermik Laboratories product insert (Jul. 2009), sanofi-aventis U.S. LLC; 10 pages.

Segura et al. "Crosslinked hyaluronic acid hydrogels: a strategy to functionalize and pattern." Biomaterials; vol. 26; pp. 359-371; 2005.

Selvi et al, "Arthritis Induced by Corticosteroid Crystals", J. Rheumatology; vol. 34:3; 1 page; 2004.

Serban et al., "Modular Extracellular Matrices: Solutions for the Puzzle"; Methods; vol. 45(1)pp. 93-98; 2008.

Shu et al., "Synthesis and evaluation of injectable, in situ crosslinkable synthetic extracellular matrices for tissue engineering"; J. Biomed. Mater. Res. A.; vol. 79(4); pp. 902-912; 2006.

Silver et al., "Physical Properties of Hyaluronic Acid and Hydroxypropylmethylcellulose in Solution: Evaluation of Coating Ability"; Journal of Applied Biomaterials; vol. 5; pp. 89-98; 1994.

Smith et al., "Five Percent Lidocaine Cream Applied Simultaneously to Skin and Mucosa of the Lips Creates Excellent Anesthesia for Filler Injections", Dermatol Surg; vol. 31; pp. 1635-1637; 2005.

Tezel et al.,, "The science of hyaluronic acid dermal fillers", J. Cosmet. Laser Ther.; vol. 10; pp. 35-42; 2008.

VISIOL, Viscoelstic gel for use in ocular surgery, (2010) p. 1, htt://www.trbchemedica.com/index.php/option=com_content&tas.

Waraszkiewicz et al., "Stability-Indicating High-Performance Liquid Chromatographic Analysis of Lidocaine Hydrochloride and Lidocaine Hydrochloride with Epinephrine Injectable Solutions", Journal of Pharmaceutical Sciences, vol. 70, No. 11, pp. 1215-1218, Nov. 1981.

Xia et al., "Comparison of Effects of Lidocaine Hydrochloride, Buffered Lidocaine, Diphenhydramine, and Normal Saline After Intradermal Injection", Journal of Clinical Anesthesia; vol. 14; pp. 339-343; 2002.

Yeom et al., "Effect of Cross-Linking Reagents for Hyaluronic Acid Hydrogel Dermal Fillers on Tissue Augmentation and Regeneration", Bioconjugate Chem., vol. 21; pp. 240-247; 2010.

Yui, et al., "Inflammation responsive degradation of crosslinked hyaluronic acid gels," Journal of Controlled Release, vol. 22; pp. 105-116; 1992.

Yui et al., "Photo-responsive degradation of heterogeneous hydrogels comprising crosslinked hyaluronic acid and lipid microspheres for temporal drug delivery," Journal of Controlled Release; vol. 26; pp. 141-145; 1993.

Yun et al., "Hyaluronan Microspheres for Sustained Gene Delivery and Site-Specific Targeting", Biomaterials, vol. 25, pp. 147-157, 2004.

Zheng Shu et al., "In situ crosslinkable hyaluronan hydrogels for tissue engineering." Biomaterials; vol. 25; pp. 1339-1348; 2004.

Zulian et al., "Triamcinolone Acetonide and Hexacetonide Intra-Articular Treatment of Symmetrical Joints in Juvenile Idiopathic Arthritis: a Double-Blind Trial", Rheumatology; vol. 43; No. 10; pp. 1288-1291; 2004.

Powell; "Stability of Lidocaine in Aqueous Solution: Effect of Temperature, pH, Buffer, and Metal Ions on Amide Hydrolysis"; Pharmaceutical Research; vol. 4, No. 1, 1987.

Cui et al; "The Comparison of Physicochemical Properties of Four Cross-Linked Sodium Hyaluronate Gels with Different Cross-Linking Agents"; Advanced Material Research; vols. 396-398; pp. 1506-1512; 2012.

Lindvall et al.; "Influence of Various Compounds on the Degradation of Hyaluronic Acid by a Myeloperoxidase System"; Chemcio-Biological Interactions; vol. 90; pp. 1-12; 1994.

Weidmann; "New Hyaluronic Acid Filler for Subdermal and Long-Lasting Volume Restoration of the Face"; European Dermatology; pp. 65-68; 2009.

* cited by examiner

Figure 1

Comparison of Conventional and Inventive Processes

Figure 2

PACKAGED PRODUCT

RELATED APPLICATIONS

This application is a divisional of U.S. patent application Ser. No. 12/125,337, filed on May 22, 2008 which claims the benefit of 35 U.S.C. §120 to U.S. Provisional Patent Application No. 60/939,664 filed on May 23, 2007, the disclosure of each of which is incorporated herein by reference.

FIELD OF THE INVENTION

The present invention relates in general to body treating compositions and methods. More specifically, the invention provides a cross-linked collagen implant of improved volume stability ("persistence") for augmenting soft tissue in mammals.

BACKGROUND OF THE INVENTION

Collagen has been used as a pharmaceutical carrier, as a surgical prosthesis (sutures and wound dressings), and as an implant material. In many instances, the collagen is cross-linked with chemical agents, radiation, or other means to improve its mechanical properties, decrease its immunogenicity, and/or increase its resistance to resorption. For example, U.S. Pat. No. 4,424,208 describes a collagen composition including cross-linked collagen and reconstituted collagen fibers having enhanced persistence. While these materials are remarkably effective, they shrink in volume after implantation due primarily to absorption of their fluid component by the body, although the shrinkage (syneresis) is less than non-cross-linked collagen. Since a constant volume or persistence is desirable, an additional injection or injections of supplemental implant material is required. It would thus be advantageous to provide collagen compositions having enhanced persistence after being introduced in vivo to a soft tissue treatment site.

SUMMARY OF THE INVENTION

The present invention relates to collagen cross-linked in a micro to non-fibrillar form and at a high concentration for augmenting soft tissue in mammals. The cross-linked collagen of the present invention has improved volume stability or persistence compared with collagen cross-linked at a neutral pH.

In one aspect, the invention features a method for preparing cross-linked collagen. The method involves the steps of obtaining micro to non-fibrillar collagen, treating the micro to non-fibrillar collagen with a cross-linking agent, and isolating cross-linked collagen. The micro to non-fibrillar collagen may be obtained by incubating fibrillar collagen in a suspension or solution of pH 2-5 or pH 9-12. In a preferred embodiment, the pH of the suspension or solution is between 4.2 and 5.0. The concentration of the micro to non-fibrillar collagen at the time of cross-linking is in the range of 3-150 mg/mL, and preferably, 38-52 mg/mL. Typically, the treating step includes treating the micro to non-fibrillar collagen with the cross-linking agent at pH 2-5 or pH 9-12, followed by treating the micro to non-fibrillar collagen with the cross-linking agent at pH 6-8 to encourage completion of the cross-linking. The method of the invention optionally may further include a step of admixing a local anesthetic agent (e.g., lidocaine) with the cross-linked collagen. Cross-linked collagen so prepared is within the invention.

Also provided in the present invention is cross-linked collagen comprising micro to non-fibrillar collagen and a cross-linking agent. The micro to non-fibrillar collagen is cross-linked by the cross-linking agent. Such cross-linked collagen may be prepared according to the method described above.

The cross-linked collagen may derive from type I, II, III, IV, or V collagen, or a combination thereof. It may also derive from telo-containing collagen, atelo-collagen, or derivatized collagen, or a combination thereof.

Preferably, the cross-linking agent is capable of forming covalent bonds between amino acid residues in the micro to non-fibrillar collagen. Examples of suitable cross-linking agents include, but are not limited to, carbodiimides, polyaldehydes, polysulfones, activated PEGs, epoxides, imidazoles, and diisocyanates. In one embodiment, the cross-linking agent is glutaraldehyde.

In some embodiments of the cross-linked type I collagen, the number of free hydroxy lysine and lysine residues per 1000 amino acid residues is in the range of 22-32, and more typically, in the range of 24-29.

The cross-linked collagen of this invention is in a gel but not fibrous state. It locks water in the gel and does not disperse like a fibrous collagen suspension. The cross-linked collagen in a gel state maintains its shape in vivo better than cross-linked collagen in a fibrous state. The fibers of the cross-linked collagen are smaller than those of fibrous collagen cross-linked at a neutral pH.

The invention further provides a composition containing the cross-linked collagen of the invention and a local anesthetic agent such as lidocaine. The local anesthetic agent is admixed with the cross-linked collagen. In addition, the invention provides a packaged product containing a syringe fitted with a needle, wherein the syringe is loaded with the cross-linked collagen of the invention.

In another aspect, the invention features a method for filling voids and defects and increasing tissue volume in a mammal. The method involves administering to a mammal the cross-linked collagen of the invention. Preferably, the cross-linked collagen is administered by intradermal or subcutaneous injection.

As used herein, "micro to non-fibrillar collagen" refers to collagen with a diameter of 5-70 nm; "fibrillar collagen" refers to collagen with a diameter of >70 nm; "fibrous collagen" refers to fibrillar collagen and larger fibers. "Telo-containing collagen" refers to collagen with intact telo peptide; "atelo-collagen" refers to collagen wherein the telo portions are removed partially or totally; "derivatized collagen" refers to chemically modified collagen. Examples of derivatized collagen include, but are not limited to, deamidated, methylated, succinylated, and phosphorylated collagen. Cross-linked collagen in a "gel state" contains micro to non-fibrillar collagen with a fiber diameter range of 5-70 nm; cross-linked collagen in a "fibrous state" contains fibrillar collagen with a fiber diameter of greater than 70 nm.

As used herein, "free hydroxyl-lysine and lysine" in collagen refers to unmodified hydroxyl-lysine and lysine; "neutral pH" refers to pH 6-8.

The present invention provides a cross-linked collagen filler for augmenting and filling soft tissue defects and voids with a material that plumps and bulks the soft tissue. The cross-linking collagen of the invention is particularly useful for deep dermal correction and sculpting. The superior shape retention makes it ideal for areas that are hard to correct and where a biocompatible bolus can provide mechanical strength to the body.

The above-mentioned and other features of this invention and the manner of obtaining and using them will become more apparent, and will be best understood, by reference to the following description, taken in conjunction with the accompanying drawings. The drawings depict only typical embodiments of the invention and do not therefore limit its scope.

DETAILED DESCRIPTION OF THE INVENTION

The present invention is based, at least in part, on the unexpected discovery that collagen cross-linked in a micro to non-fibrillar state and preferably at a high concentration has improved persistence compared to collagen cross-linked at a neutral pH.

More specifically, fibrillar collagen is fairly porous and allows the transport of cells and large molecules. By cross-linking smaller fiber (microfibrillar) collagen, more rigidity within the network was created to further increase the diffusion hindrance (Rosenblatt and Shenoy, 1993, Chain Rigidity and Diffusional Release in Biopolymer Gels, Proceed Intern Symp Control Rel Bioact Mater 20, Controlled Release Society, Inc.). While fibrillar collagen matrices are capable of moderating the diffusion of large molecules, smaller fiber and non-fibrillar collagen can modulate the diffusion of smaller molecules (Rosenblatt et al., 1989, The Effect of Collagen Fiber Size Distribution on the Release Rate of Protein from Collagen Matrices by Diffusion, *J Controlled Release* 9:195-203). Cross-linked micro-fibrillar collagen has a tighter network or mesh, which creates a collagen matrix more resistant or persistent to biological degradation. In the present invention, as described in the Example below, type I collagen matrices were modified to reduce the penetration of cells and proteins into the matrices.

The present invention is particularly directed to the filling of voids and defects and increasing tissue volume in mammals with injectable cross-linked Type I/III collagen implants. Accordingly, the invention provides a method for preparing cross-linked collagen by cross-linking collagen in a micro to non-fibrillar state and preferably at a high concentration.

The cross-linked collagen of the present invention primarily derives from mammalian source materials, such as bovine or porcine corium, although human placenta material, collagen produced from human fibroblast cell culture, or recombinantly produced collagen expressed from a cell line may also be used. The donor need not be genetically similar to the host into which the material is ultimately implanted.

Figure 1:
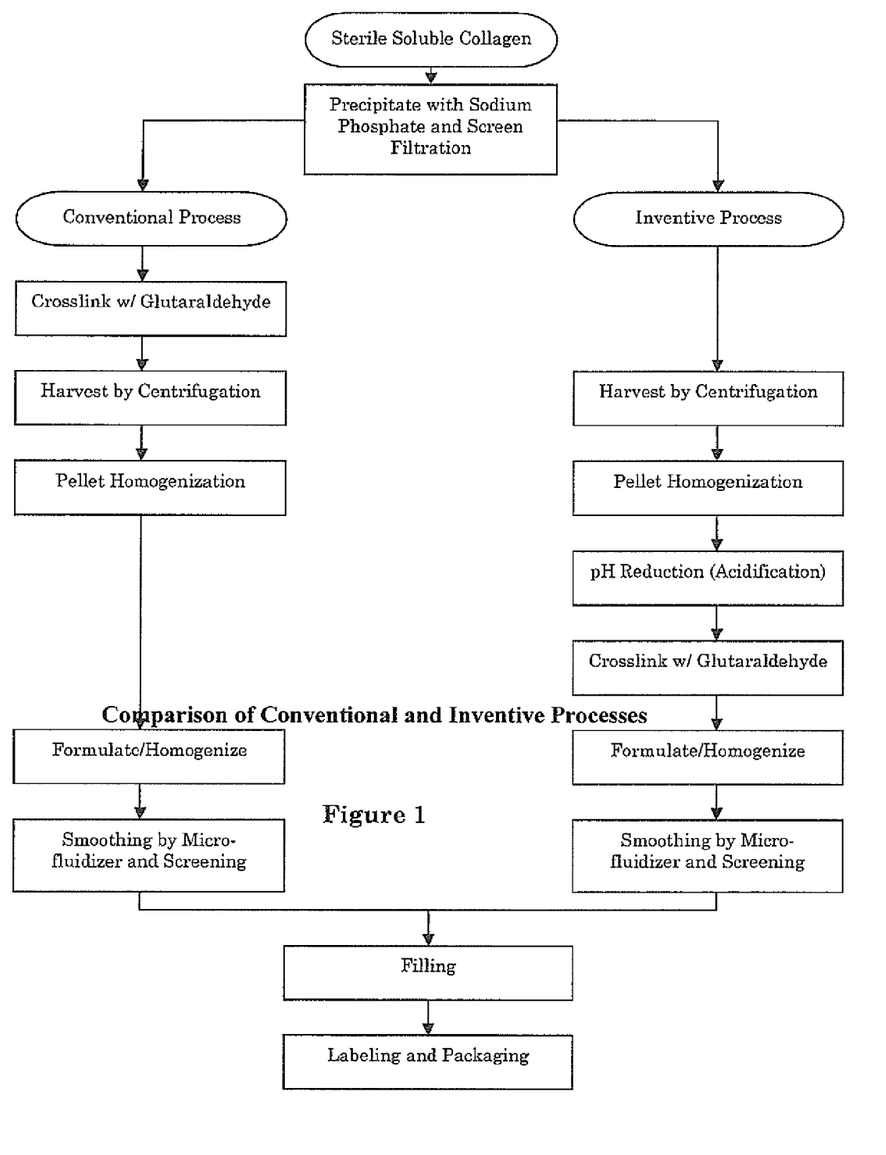
FIG. 1 is a flow chart illustrating representative conventional and inventive processes for preparation of cross-linked collagen.

Referring to FIG. 1, in a conventional process, purified, type I, pepsin digested human collagen from Allergan Medical Biomaterials (48490 Milmont Drive, Fremont, Calif. 94538) is reconstituted from a solution by neutralizing the solution at reduced temperatures and ionic strengths hypotonic relative to physiological conditions. The pH of the solution is raised to a level at which the collagen in solution reaggregates into fibrils. The reconstituted fibrous collagen is cross-linked with a cross-linking agent at a neutral pH. The cross-linked collagen is then harvested by centrifugation, formulated/homogenized, smoothed, and screened.

In contrast, the process of the present invention involves concentrating the collagen suspension by centrifugation. The pellet is homogenized, and the pH is adjusted to a non-neutral level prior to cross-linking. The collagen concentration at the time of cross-linking is usually in the range of 3-150 mg/mL, more typically 30-60 mg/mL, 35-55 mg/mL, or 38-52 mg/mL. The pH is adjusted to a non-neutral level appropriate for the cross-linking agent to be used. For example, the pH may be adjusted to about 4.5 for cross-linking by glutaraldehyde or to about 10 for cross-linking by divinylsulfone. A dilute solution of HCl or the like is typically added to adjust the pH to a desired acidic level, while NaOH or the like is used for adjusting the pH to a desired alkaline level.

The cross-linking begins at pH 2-5 or pH 9-12, more preferably at pH 2-3, 2-4, 3-4, 3-5, or 4-5, or pH 9-10, 9-11, 10-11, 10-12, or 11-12. At these pH ranges, the collagen fiber is unraveled to a micro to non-fibrillar state. More lysine groups are exposed and available for cross-linking. In addition, a high collagen concentration increases the reaction rate. The collagen is stabilized while being cross-linked into small fiber structures. Preferably, after the initial cross-linking, the pH is further adjusted to a neutral pH, e.g., pH 6-8, using 0.5 M phosphate, pH 11.2, or the like, to encourage complete cross-linking. The pH can then be adjusted back to neutral without causing the cross-linked collagen gel to collapse or to spontaneously form fibers.

Usually a cross-linking agent is polyfunctional, and more usually bifunctional. The cross-linking conditions of the present invention are such as to produce covalently cross-linked collagen that has improved persistence relative to an implant of a comparable formulation prepared according to the conventional process. When this degree of cross-linking has been reached, the cross-linking reaction is optionally quenched by adding a quenching agent. The quenching agent forms a water soluble adduct with the cross-linking agent. The concentration of the collagen in the suspension at the time of cross-linking, the concentration of the cross-linking agent, and the duration of the cross-linking reaction are important process conditions for obtaining the kind and degree of cross-linking that provides a product having enhanced persistence.

The collagen can be cross-linked by any of a number of conventional chemical cross-linking agents, including, but not limited to, glutaraldehyde, divinylsulfone, epoxides, carbodiimides, imidazole, N-hydroxy-succinimide (NHS), thiol derivatized polyethylene glycol (PEG), and the like.

Aldehydes are preferred cross-linking agents. Examples of aldehydes that may be used to cross-link collagen are formaldehyde, acetaldehyde, glyoxal pyruvic aldehyde, and dialdehyde starch. Glutaraldehyde is particularly preferred. Compounds that have functional groups that react with the functional groups of the cross-linking agent (e.g., aldehyde group) to form water soluble adducts may be used to quench the cross-linking reaction. Quenching agents that have free amino groups such as amino acids are preferred. Glycine is particularly preferred. The concentration of glutaraldehyde in the reaction mixture is typically about 0.001% to about 0.05% by weight. The glutaraldehyde reacts with hydroxy lysine and lysine residues of the collagen fibers, thereby reducing the number of free hydroxy lysine and lysine in the collagen. At the glutaraldehyde concentrations mentioned above, the number of free hydroxy lysine and lysine residues per 1000 amino acid residues after cross-linking is about 22-32, more typically about 24-29. Hydroxy lysine and lysine content may be measured by reducing the cross-linked collagen with borohydride and hydrolyzing the reduced material under vacuum in 5.7 N HCl for 24 hours at 100° C. Amino acid analysis may be performed with available analyzers (e.g., a Durrum Model D-500 analyzer) and the hydroxy lysine and lysine residues quantified by comparing the hydroxy lysine and lysine/alanine ratio to those observed in non-cross-linked controls.

The duration of the cross-linking reaction is usually in the range of one-half hour to about one week. The reaction is normally carried out at about 10° C. to about 35° C. The quenching agent is added in at least stoichiometric proportions relative to the cross-linking agent.

A particularly preferred cross-linking protocol is about 38 to about 52 mg/mL collagen concentration, pH about 4.2 to about 5.0, and about 0.01% by weight glutaraldehyde for about 16 hours at approximately 22° C.

After the cross-linking reaction has been terminated, the cross-linked collagen product may be washed with an aqueous buffer solution to remove unreacted aldehyde, aldehyde polymers, and, if quenching was employed, unreacted quenching agent, and aldehyde-quenching agent adducts. A sodium phosphate-sodium chloride buffer solution, pH 6.9 to 7.4, is preferred. The washed product may be concentrated, such as by filtration or centrifugation, to a suitable protein concentration range, typically about 20 to about 65 mg/mL, more usually about 25 to about 40 mg/mL. Protein concentration may be adjusted to this range by addition of buffer or further concentration, as the case may be. The washed product has a free aldehyde content below about 20 ppm.

Formulation of the cross-linked collagen typically involves adjusting the ionic strength to isotonicity (i.e., about 0.15 to about 0.2) and adding a local anesthetic, such as lidocaine, to a concentration of about 0.3% by weight to reduce local pain upon injection. A particularly preferred cross-linking product has a collagen concentration of 30.0-37.0 mg/mL, a lidocaine concentration of 2.7-3.3 mg/mL, and a pH of 7.0-7.6. The cross-linked product is further homogenized, smoothed by microfluidization, and screened by forcing the collagen fibers through a screen of defined pore size.

The cross-linked collagen is then loaded into syringes fitted with a #25 gauge or larger gauge needle for injection. In the case of formulations used for dermal augmentation, the term "injectable" means that the formulation can be dispensed from syringes having a gauge as low as #25 under normal manual pressure without substantial spiking.

The above described steps for preparing the inventive cross-linked collagen are preferably carried out in sterile conditions using sterile materials.

The cross-linked collagen of the present invention may be injected intradermally or subcutaneously to augment soft tissue, to repair or correct congenital anomalies, acquired defects or cosmetic defects. Examples of such conditions are congenital anomalies such as hemifacial microsomia, malar and zygomatic hypoplasia, unilateral mammary hypoplasia, pectus excavatum, pectoralis agenesis (Poland's anomaly), and velopharyngeal incompetence secondary to cleft palate repair or submucous cleft palate (as a retropharyngeal implant); acquired defects (post traumatic, post surgical, or post infectious) such as depressed scars, subcutaneous atrophy (e.g., secondary to discoid lupis erythematosus), keratotic lesions, enophthalmos in the enucleated eye (also superior sulcus syndrome), acne pitting of the face, linear scleroderma with subcutaneous atrophy, saddle-nose deformity, Romberg's disease, and unilateral vocal cord paralysis; and cosmetic defects such as glabellar frown lines, deep nasolabial creases, circum-oral geographical wrinkles, sunken cheeks, and mammary hypoplasia.

In particular, the invention provides a soft tissue augmentation injectable that fills the space with a durable strong biocompatible bulking agent. Compared to the conventional cross-linked collagen, the collagen fiber of the present invention is reduced in size and forms a network that takes up more space. The inventive cross-linked collagen is elastic and resilient. It keeps its shape over time and resists breakdown and cellular infiltration.

The following example is intended to illustrate, but not to limit, the scope of the invention. While such example is typical of those that might be used, other procedures known to those skilled in the art may alternatively be utilized. Indeed, those of ordinary skill in the art can readily envision and produce further embodiments, based on the teachings herein, without undue experimentation.

EXAMPLE

Preparation of Inventive Cross-Linked Collagen

Purified, type I, pepsin digested human collagen from Allergan Medical Biomaterials (48490 Milmont Drive, Fremont, Calif. 94538) was precipitated by raising the pH to 7.0-7.6 and then centrifuging at 17000×g for 5-7 minutes. The supernatant was aseptically decanted from the centrifuge bottle, and the collagen pellet aseptically suctioned into a homogenization vessel. The precipitated collagen was aseptically homogenized. The protein concentration was 91.6 mg/mL.

0.05 M HCl buffer and sterile filtered WFI (water for injection) were mixed with the homogenate. The protein concentration was 44.6 mg/mL; the pH was 4.8.

3000 ppm glutaraldehyde buffer was mixed with the acid homogenate. The mixture was allowed to incubate for 1.5 hours and remixed, further incubated for 23 hours and remixed, and incubated again for 72 hours and remixed. The protein concentration was 37.1 mg/mL; the pH was 4.6.

The cross-linked homogenate was mixed with 0.5 M sodium phosphate buffer, pH 11.2, followed by 0.04 M sodium phosphate/2.6 M sodium chloride/60 mg/mL lidocaine buffer. The homogenate was allowed to incubate for 24 hours and remixed. The protein concentration was 31.9 mg/mL. The formulated homogenate was then passed through a microfluidizer and screened.

Comparison of Conventional and Inventive Cross-Linked Collagen

The conventional cross-linked collagen was obtained by precipitating and cross-linking purified, type I, pepsin digested human collagen from Allergan Medical Biomaterials (48490 Milmont Drive, Fremont, Calif. 94538) at about 3 mg/mL and a neutral pH. The conventional cross-linked collagen was harvested by centrifugation, and then homogenized, formulated, smoothed using microfluidization and screened. The inventive cross-linked collagen was obtained by precipitating purified, type I, pepsin digested human collagen from Inamed Biomaterials (48490 Milmont Drive, Fremont, Calif. 94538) at about 3 mg/mL at a neutral pH and harvesting the collagen by centrifugation. The pH was reduced to 4.4-4.8, and the collagen was cross-linked. The inventive cross-linked collagen was then homogenized, formulated, smoothed using microfluidization, and screened.

The biocompatibility of the inventive cross-linked collagen was tested and compared to that of the conventional cross-linked collagen. Safety was assessed through a cytotoxicity study and multiple rabbit subcutaneous implantation studies. The data demonstrates that the inventive cross-linked collagen, like the conventional cross-linked collagen, was biocompatible.

More specifically, the cytotoxicity study was performed using the ISO Elution Method. The inventive cross-linked collagen implants caused no cell lysis or toxicity (Table I).

TABLE I

Cytotoxicity Study of the Conventional and Inventive Cross-linked Collagen Implants

| | Confluent Monolayer | Percent Rounding | Percent Cells without Intracytoplasmic Granules | Percent Lysis | Grade | Reactivity |
|---|---|---|---|---|---|---|
| Conventional | 0 | 0 | 0 | 0 | 0 | None |
| Inventive | 0 | 0 | 0 | 0 | 0 | None |

The rabbit subcutaneous implantation assay was used to compare tissue responses to the conventional and inventive cross-linked collagen implants at several different timepoints. The tissue response to the inventive implant was similar to that seen with the conventional implant (Table II). The microscopic scores ranging from non-irritant to slight irritant are within the range of acceptable variability and considered to be satisfactory.

TABLE II

Rabbit Implantation Evaluation

| Time Points | Conventional | Inventive |
|---|---|---|
| 1 week | Non-irritant | Non-irritant |
| 4 weeks | Non-irritant | Slight irritant |
| 9 weeks | Not tested | Not tested |
| 12 weeks | Non-irritant | Slight irritant |

A rat subcutaneous implantation study was performed to compare the persistence of the inventive cross-linked collagen implant relative to the conventional cross-linked collagen implant. As part of the rat implantation study, a macroscopic evaluation of the implant site was performed. There was no capsule formation or adverse reaction for either implant for all time points studied (Table III).

TABLE III

Rat Subcutaneous Macroscopic Evaluation

| Time Points | Conventional | Inventive |
|---|---|---|
| 4 weeks | No capsule formation or adverse reaction | No capsule formation or adverse reaction |
| 9 weeks | No capsule formation or adverse reaction | No capsule formation or adverse reaction |
| 13 weeks | No capsule formation or adverse reaction | No capsule formation or adverse reaction |
| 24 weeks | No capsule formation or adverse reaction | No capsule formation or adverse reaction |

To assess effectiveness, the persistence of the inventive relative to the conventional cross-linked collagen was evaluated using wet weight recovery in conjunction with shape retention in the rat subcutaneous model (McPherson et al., 1988, Development and Biochemical Characterization of Injectable Collagen, *J Dermatol Surg Oncol* 14, Suppl 1). Shape retention is considered to be good measurement of the collagen implant's ability to maintain wrinkle correction. If the implant cannot maintain its shape, it may not correct a wrinkle effectively.

Figure 2:
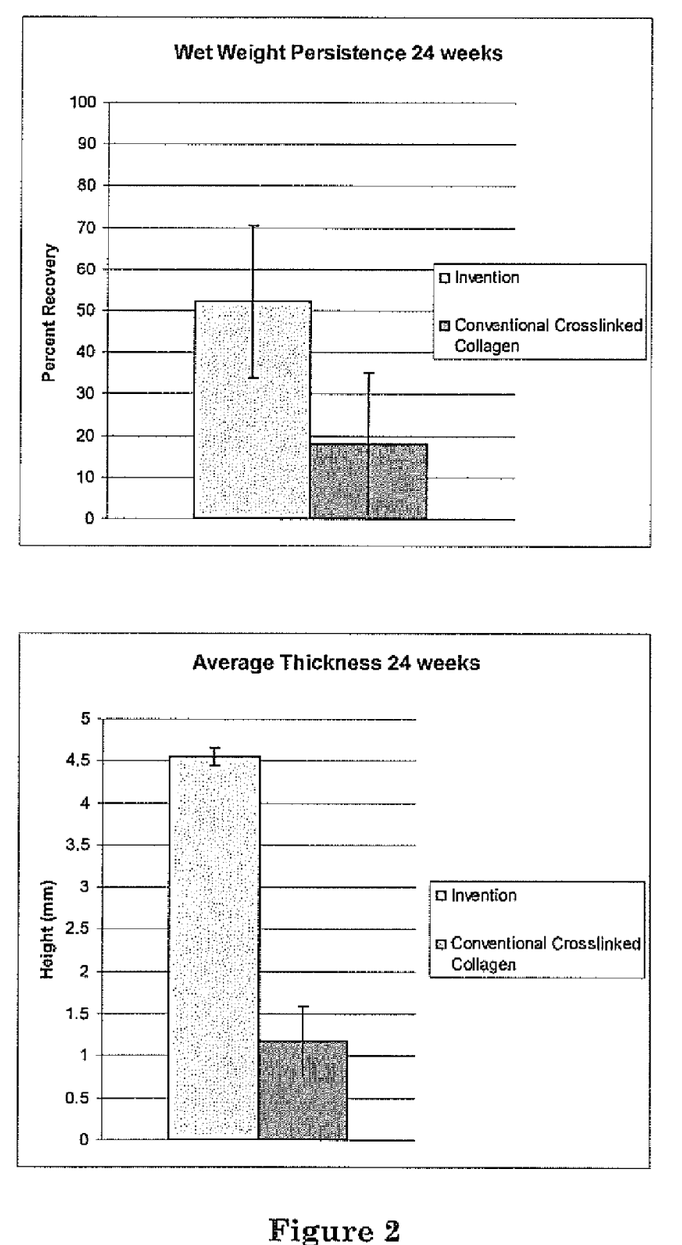
FIG. 2 shows the persistence of the inventive cross-linked collagen relative to the conventional cross-linked collagen.

The data from the rat subcutaneous studies, summarized in FIG. 2, indicates that the inventive implant, on average, had greater wet weight recovery and maintained its height better than the conventional implant after 24 weeks of implantation.

All patents and articles cited herein are incorporated by reference in their entirety.

What is claimed is:

1. A packaged product useful for dermal correction and sculpting comprising:
   a syringe; and
   an injectable dermal filler composition in the syringe, the composition comprising a cross-linked collagen prepared by the steps of
   incubating collagen selected from a group consisting of type I collagen, type II collagen, type III collagen, type IV collagen, type V collagen, telo-containing collagen, atelo-collagen, derivatized collagen, and a combination thereof, in a suspension or solution having pH in the range of pH 2-5 or pH 9-12,
   treating said collagen with a cross-linking agent selected from the group consisting of carbodiimides, polyaldehydes, polysulfones, activated PEGs, epoxides, imidazoles and diisocyanates at pH 2-5 or pH 9-12, and
   isolating the cross-linked collagen to thereby obtain the composition,
   wherein the cross-linked collagen is in a gel but not in a fibrous state.

2. The packaged product of claim 1, wherein the cross-linking agent is glutaraldehyde.

3. The packaged product of claim 1, wherein the cross-linked collagen locks water in the gel and does not disperse like a fibrous collagen suspension.

4. The packaged product of claim 1, wherein the fibers of the cross-linked collagen are smaller than those of fibrous collagen cross-linked at a neutral pH.

5. The packaged product of claim 1, wherein a concentration of the collagen in the composition is in the range of 3 mg/mL-150 mg/mL.

6. The packaged product of claim 1, wherein a concentration of the collagen in the composition is in the range of 38 mg/mL-52 mg/mL.

7. The packaged product of claim 1, wherein the composition further comprises a local anesthetic agent admixed with the cross-linked collagen.

8. The packaged product of claim 7, wherein the local anesthetic agent is lidocaine.

9. The packaged product of claim 1, wherein the incubating step comprises incubating the collagen in a suspension or solution of pH 4.2-5.0.

10. The packaged product of claim 1, wherein the treating step further comprises treating the collagen with the cross-linking agent at pH 6-8.

11. The packaged product of claim 1, wherein the pH of the suspension or solution containing the collagen is in the range of pH 4.2-5.0.

12. The packaged product of claim 1, wherein the process for preparing the composition further comprises washing the crosslinked collagen with an aqueous buffer solution having a pH of 6.9 to 7.4.

* * * * *

UNITED STATES PATENT AND TRADEMARK OFFICE
CERTIFICATE OF CORRECTION

PATENT NO. : 8,338,375 B2
APPLICATION NO. : 12/649020
DATED : December 25, 2012
INVENTOR(S) : Jacqueline Anne Schroeder et al.

It is certified that error appears in the above-identified patent and that said Letters Patent is hereby corrected as shown below:

On the title page, in column 2, in item (56), under "Other Publications", line 4, delete "Sponse:" and insert -- Sponge: --, therefor.

On the title page, in column 2, in item (56), under "Other Publications", lines 9-10, delete "Charaterization" and insert -- Characterization --, therefor.

On the title page, in column 2, in item (56), under "Other Publications", line 19, delete "Dematologic" and insert -- Dermatologic --, therefor.

Title page 3, in column 1, in item (56), under "Other Publications", line 14, delete ""Hyroxyethyl" and insert -- "Hydroxyethyl --, therefor.

Title page 3, in column 1, in item (56), under "Other Publications", line 16, delete "(JUVADERM)" and insert -- (JUVEDERM) --, therefor.

Title page 3, in column 1, in item (56), under "Other Publications", line 57, delete "Chrondrocytes" and insert -- Chondrocytes --, therefor.

Title page 3, in column 2, in item (56), under "Other Publications", line 27, delete "Gonarthosis:" and insert -- Gonarthrosis: --, therefor.

Title page 3, in column 2, in item (56), under "Other Publications", line 31, delete "[Acta" and insert -- Acta --, therefor.

Title page 3, in column 2, in item (56), under "Other Publications", line 37, delete "An Theum" and insert -- Ann Rheum --, therefor.

Title page 3, in column 2, in item (56), under "Other Publications", line 60, delete "Institue" and insert -- Institute --, therefor.

Title page 3, in column 2, in item (56), under "Other Publications", line 64, delete "Slerotomy" and insert -- Sclerotomy --, therefor.

Signed and Sealed this
Seventh Day of October, 2014

Michelle K. Lee
*Deputy Director of the United States Patent and Trademark Office*

CERTIFICATE OF CORRECTION (continued)
U.S. Pat. No. 8,338,375 B2

Title page 4, in column 1, in item (56), under "Other Publications", line 6, delete "Rheuymatism;" and insert -- Rheumatism; --, therefor.

Title page 4, in column 1, in item (56), under "Other Publications", line 7, delete ""Evlaution" and insert -- "Evaluation --, therefor.

Title page 4, in column 1, in item (56), under "Other Publications", line 9, delete "Chartacterization"; Plastric" and insert -- Characterization"; Plastic --, therefor.

Title page 4, in column 2, in item (56), under "Other Publications", line 3, delete "Viscoelstic" and insert -- Viscoelastic --, therefor.

Title page 4, in column 2, in item (56), under "Other Publications", line 3, delete "htt://" and insert -- http:// --, therefor.

Title page 4, in column 2, in item (56), under "Other Publications", line 40, delete ""Influcence" and insert -- "Influence --, therefor.

Title page 4, in column 2, in item (56), under "Other Publications", lines 41-42, delete "Chemcio-Biological" and insert -- Chemico-Biological --, therefor.